United States Patent [19]
Chiang et al.

[11] Patent Number: 4,935,535
[45] Date of Patent: Jun. 19, 1990

[54] ULTRAVIOLET-AUTOCURABLE BENZOPHENONE TETRACARBOXYLIC DIANHYDRIDE-BASED POLYURETHANE ACRYLATE OLIGOMERS

[75] Inventors: Wen-Yen Chiang; Shao-Ching Chan, both of Taipei, Taiwan

[73] Assignee: National Science Council, Taipei, Taiwan

[21] Appl. No.: 299,072

[22] Filed: Jan. 19, 1989

[51] Int. Cl.$^5$ ........................................... C07C 125/07
[52] U.S. Cl. .................................................... 560/26
[58] Field of Search .......................................... 560/26

[56] References Cited

U.S. PATENT DOCUMENTS 4,782,175  11/1988  Wehowsky et al. .................. 560/26

FOREIGN PATENT DOCUMENTS 0037314  10/1981  European Pat. Off. ............. 560/26
1328232   8/1973  United Kingdom .................. 560/26

Primary Examiner—Bruce Gray
Attorney, Agent, or Firm—Bacon & Thomas

[57] ABSTRACT

The present invention provides an ultraviolet-autocurable benzophenone tetracarboxylic dianhydride-based polyurethane acrylate oligomer.

5 Claims, No Drawings

ULTRAVIOLET-AUTOCURABLE BENZOPHENONE TETRACARBOXYLIC DIANHYDRIDE-BASED POLYURETHANE ACRYLATE OLIGOMERS

BACKGROUND OF THE INVENTION

The present invention relates to ultraviolet-autocurable oligomers. More particularly it relates to acrylo-urethane oligomers having built-in benzophenone type photo-initiators, which are auto-curable through ultraviolet (UV) light radiation.

Since the development of high intensive radiation processing such as ultraviolet (UV) light and electron beams as an alternative to heat processing, photo-curable resins are now widely used for coating, printing, adhesion, and photo-imaging. In general, for fast and efficient curing of such resins, it is necessary to include a relative large amount of the initiating component within the system. However, such levels of photo-initiator can not be used in certain system where high levels of photo-initiator do not dissolve or mix homogenously.

U.S. Pat. No. 4,004,998 discloses a photo-polymerizable compound having built-in sensitizers which is auto-polymerizable through UV radiation. Since the photo-initiators are incorporate within the polymerizable system through a chemical reaction between the photo-initiator and the polymerizable monomer, the compatibility problem that results by merely physically mixing the photo-initiators with the polymerizable monomers is prevented. The photo-polymerizable compound disclosed in the above U.S. Patent comprises the product of the reaction of a monomeric hydroxy-containing polyethylenically unsaturated ester or a monomeric isocyanate-modified hydroxy-containing polyethylenically unsaturated ester and a monocarboxy-substituted benzophenone, e.g. benzophenone tetracarboxylic dianhydride (BTDA). However, in Example 19 thereof the monoethylenically unsaturated esters having free hrdroxyl groups were demonstrated to be particularly not acceptable for preparing the photopolymerizable product because the speed of curing was too slow, the viscosity of the solution was too high, and the surface properties were poor. As well known to those skilled in the art, the polymeric coating prepared from a monomeric compound will have a poorer surface properties compared to the one prepared from a resin.

U.S. Pat. No. 3,759,809 discloses an isocyanate-modified polyethylenically unsaturated ester having free hydroxyl groups, which is mixed with a photo-initiator to provide a photopolymerizable composition having reduced water sensitivity and reduced toxicity. This isocyanate-modified polyethylenically unsaturated ester is a reaction product of a polyethylenically unsaturated ester having free hydroxyl groups formed by the reaction of an ethylenically unsaturated acid and a polyhydric alcohol with an organic isocyanate. However, the inventors in Example 18 demonstrated that an isocyanate-modified product, where the starting ester was monoethylenically unsaturated, was not accepted because the speed of curing was too slow, the viscosity of the solution was too high, and the surface properties were poor. Furthermore, in Example 19 an isocyanate-modified product, where the starting ester was reacted with sufficient phenyl isocyanate to convert all of the hydroxyl groups to carbamate groups, was found not acceptable as a lithographic ink vehicle because of stripping. Basically, the composition of this U.S. Pat. No. 3,759,809 still suffers the conventional incompatibility problem between the resin and the photo-initiator and instability in storage.

SUMMARY OF THE INVENTION

The present invention provides an UV-curable BTDA-based polyurethane acrylate oligomer, which contains a weight ratio of BTDA to the oligomer ranging from 1:6 to 1:10. The BTDA-based polyurethane acrylate oligomer is prepared by reacting a reaction product of BTDA and a hydroxy-terminate polyol, having a number-average molecular weight ranging from 400–800, with 2,4-toluene diisocyanate to form an isocyanate-capped intermediate and then reacting the intermediate with an acrylate containing a free hydroxyl group.

An alternative process may be used to prepare the BTDA-based polyurethane acrylate oligomer by reacting a reaction product of BTDA and the polyol with a reaction product of the 2,4-toluene diisocyanate and the acrylate.

The BTDA-based polyurethane acrylate oligomer product has the following general formula:

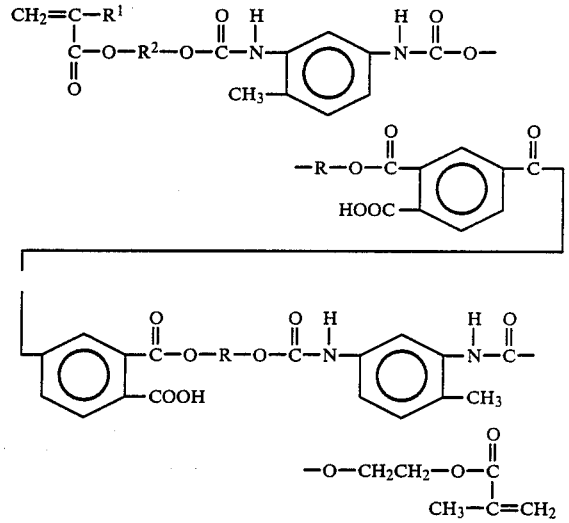

where
- $R^1$ is hydrogen or a methyl group, preferably a methyl group;
- $R^2$ is a $C_1$–$C_4$ alkyl group; and
- R represents the R in the polyols, HO—R—OH, having the following formulas

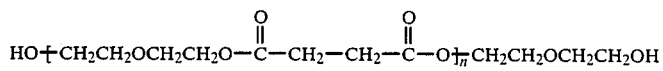

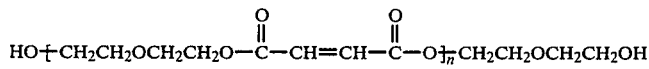

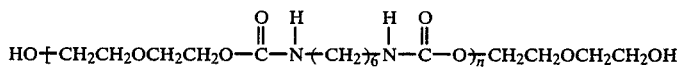

in which n is the number-average molecular weight ranging from 300–800.

The auto-curable oligomers provided in the present invention possess good pot life and are cured rapidly when exposed to UV radiation without the addition of photo-initiator. The different polyols are used to obtain cured products with wide range of mechanical properties. For various practical application, the auto-curable oligomers may be further mixed with reactive monomer(s) to bring the system to a different working viscosity at room temperature.

DETAILED DESCRIPTION OF THE PREFERRED EMBODIMENTS

Example 1:

Synthesis of Various Polyols:

Synthesis of Polydiethylene maleate (UES) and Polydiethylene Succinate (SES)

A four-necked flask was equipped with a magnetic stirrer, condenser, thermometer and nitrogen inlet. In the flask was placed diethylene glycol and anhydride (maleic anhydride or succinic anhydride) with a molar ratio of glycol and anhydride at 2.3:1. The mixture was heated at 120 C. for 3 hrs and then at 190° C.–200° C. for another 15 hrs. Water was formed from the condensation reaction was continuously distilled from the reactor. After the acid number reached below 5, the mixture was distilled to remove the unreacted materials under reduced pressure. The resulting polydiethylene maleate, designated UES for unsaturated oligoester, was a slightly yellowish transparent viscous liquid, with a molecular weight of about 472 determined by end-group titration analysis (acid number, 3.6 and hydroxyl number, 230.5). The polyethylene succinate, designated SES for saturated oligoester, was a colorless transparent viscous liquid, with a molecular weight of about 427 (acid number, 3.85 and hydroxyl number, 255). The molecular weight was calculated from the following equation:

corrected hydroxyl No. = acid No. + hydroxyl No.

$$\text{Molecular Weight} = \frac{2 \times 56.1 \times 1000}{\text{acid No.} + \text{corrected hydroxyl No.}}$$

Synthesis of Polydiethylene hexamethylenedicarbamate (SPU)

A four-necked flask was equipped with a magnetic stirrer, condenser, thermometer and pressure-equalizing dropping, and nitrogen inlet. The flask charged with diethylene glycol was heated to 90° C., and then hexamethylene diisocyanate was added dropwise with the molar ratio of glycol and diisocyanate at 2.4:1. After the addition was completed, the mixture was heated at 120° C. for 2 hrs. The product was purified by washing three times with anhydrous methanol and dried under vacuum. The resulting polydiethylene hexamethylenedicarbamate, designated SPU for saturated polyurethane, was a white solid at room temperature, and the yield was about 84%.

Example 2:

Synthesis of BTDA-based autocurable polyurethane methacrylate olygomers:

2-hydroxyethyl methacrylate (HEMA)-capped polyurethane-methacrylate oligomers based on BTDA were synthesized according to the following scheme I:

Scheme I

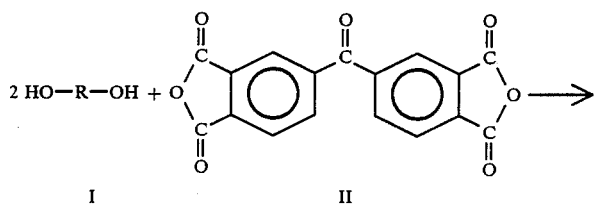

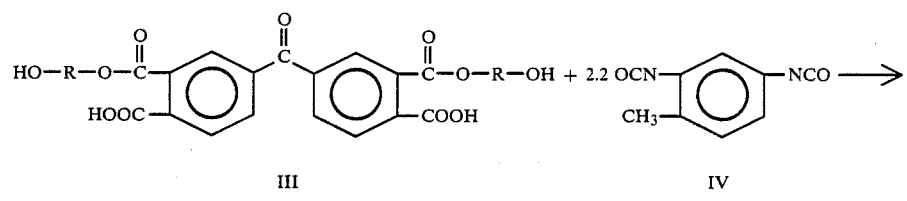

-continued
Scheme I

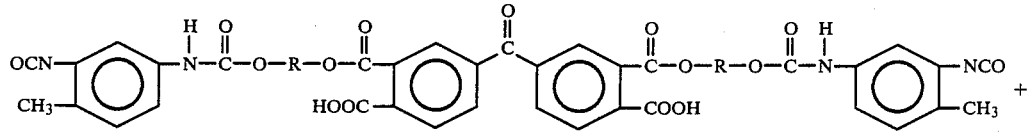

V

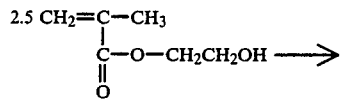

VI

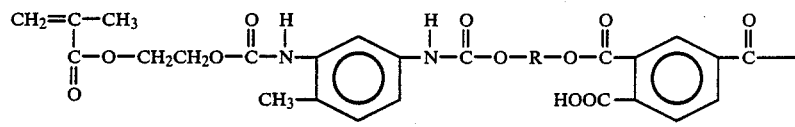

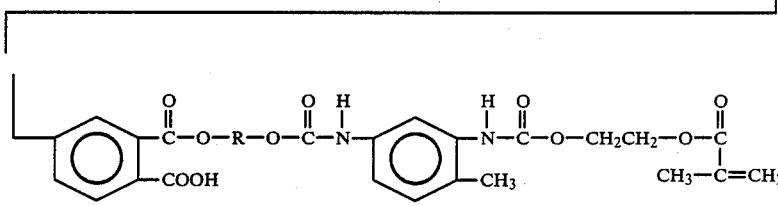

VII

In the first step, 0.3 mole of polyol (I:120g of polyethylene glycol (PEG) (having a number average molecular weight of about 400), 128.1g of SES, 141.6g of UES or 114.1g or SPU) was reacted with 0.15 mole of benzophenone tetracarboxylic dianhydride (II, 48.3g) under nitrogen atmosphere for 2 hrs at 100° C. and for another 1 hr at 120° C. The mixture, a transparent viscous liquid, was cooled at room temperature. In the second step, the half-ester adduct of polyol and BTDA (III) was reacted with 0.33 mole of 2,4-toluene diisocyante (IV,57.5g) in tetrahydrofuran (100 mL), THF, under nitrogen with stannous octoate as catalyst. The solution was sucessively stirred for 3 hrs at 40° C. and then heated to 60° C. to force the reaction to completion. In the third step, the isocyante-capped intermediate (V) was reacted with 0.38 mole of HEMA (VI, 49.5g) in the presence of hydroquinone under air for 5 hrs at 65° C. Each reaction was undertaken in the same flask as the first step without isolation. The completion of the reaction were confirmed by the disappearance of the peak caused by N=C=O stretching absorption near 2280 cm$^{-1}$ by IR. The resulting auto-curable oligomer (VII) was designated as UM-PEG, UM-SES, UM-UES, or UM-SPU according to the polyol used.

Measurement of Various Properties and Results

Photocuring

Prepared oligomers were cast between two Mylar films and irradiated by a high-pressure mercury lamp (Model USH-500D manufactured by Ushio Electric Co., Japan) at a distance of 30 cm for various lengths of time.

Pot Life

Oligomers were put into an aging oven for a week at various temperature, and then extracted by THF to determine their gel content.

Gel Content

Oligomers after photocuring or thermocuring were extracted by THF at 60° C. for 12 hrs and residual polymers were dried and weight.

Molecular Weight

Oligomers (0.5 wt%) in THF solution were injected 10μL into a Shimadzu Liquid Chromatography Model LC-5A that was equipped with an UV detector (model SPD-2A, wavelength 254 nm, range 128) and RI detector (Toyo Soda, Model RI-8000, range 256). The columns used were TSK-G1000HXL, TSK-G2000HXL and TSK-G3000HXL, at room temperature with a flow rate of 1 mL/min and pressure below 50 kg/cm$^2$. The calibration curve was plotted by using monodisperse polystyrene and hydroquinone.

Tensile Properties

Cured films were cut into 50×60 mm strips. After conditioning for 24 hrs at room temperature, the specimen was clamped in an Instron Testing Machine, Model 1130, with a jaw separation of 2 cm and extended at a rate of 5 cm/min to failure. The tensile strength, Young's modulus, and elongation at break were determined from the load extension diagram.

The fundamental properties of these autocurable oligomers such as the number average molecular weight obtained from GPC, viscosities, pH, and solubilities of prepared oligomers are listed in Table I.

These autocurable oligomers must be activated by radiation, such as ultraviolet light, electron beam, and gamma radiation. At the same time they also must be inactive at ambient temperatures to provide storage and handling stability. To evaluate this properties, autocurable oligomers were baked in an aging oven at 120–180° C. using four different temperatures for a week. Also, the autocurable oligomers were cured directly by UV without the addition of any photo-initiators. The curing process was carried through a transparent Mylar film to prevent any reaction with oxygen. If the covering film was removed immediately after 3 sec of irradiation, the resin remained sticky, and the gel content was below 80%. However, if the film was removed 2 hrs after the irradiation (this process is defined as postcuring), the surface of the cured oligomer was hard and smooth, and its gel content was greater than 90%. All the cured films possess good thermal stability and the mojor deposition temperature are all above 290° C.

TABLE I

| Properties | UM-PEG | UM-SES | UM-UES | UM-SPU |
|---|---|---|---|---|
| M | 2060 | 2470 | 2610 | 2210 |
| Viscosity (cp) | 23250 | 25700 | 28100 | 35500 |
| pH Value | 4.5 | 5.0 | 5.8 | 4.5 |
| Solubility | (Dissolves in acetone, chloroform, dioxane, THF; insoluble in BTX, alcohols, cyclohexane, CCl) | | | |
| Color | (All are transparent yellowish-brown) | | | |
| Wt % of unreacted HEMA* | 4.5 | 2.7 | 2.5 | 5.2 |

*Wt % of unreacted HEMA in resin is measured from the GPC chromatogram.

Inorder to determine the curing rates of several autocurable oligomers, the gel content of cured films was determined immediately after irradiation without passing the postcuring process. The results are listed in Table II. All oligomers are cured rapidly within 1 sec and then levelled off in 6 sec. From Table II we also see that all the oligomers possess good pot life below 140° C. without gelation.

TABLE II

| | Gel Content, % | | | | | | | | | |
|---|---|---|---|---|---|---|---|---|---|---|
| | Baking Temperature (°C.) | | | | Irradiation Time (s) | | | | | |
| | 120 | 140 | 160 | 180 | 1 | 3 | 10 | 20 | 30 | 40 |
| UM-PEG | 0 | 0 | 63.5 | 77.4 | 70 | 80 | 83 | 84.5 | 84.7 | 86.5 |
| UM-SES | 0 | 0 | 82 | 98 | 64.7 | 68.8 | 71 | 74 | 75 | 75.5 |
| UM-UES | 0 | 81 | 90 | 99 | 60 | 63 | 64.5 | 65 | 67 | 70 |
| UM-SPU | 0 | 0 | 50 | 70 | 64.7 | 70.6 | 72 | 78 | 80 | 81 |

These autocurable oligomers were found to be better than the photocurable resins that were prepared using benzoin ethyl ether as the initiator in terms of gel content and curing rate. The photocurable resins are disclosed in our provions paper entitled "Preparation and Properties of Photocurable Unsaturated Oligoster Acrylourethanes", J. Appl. Polym. Sci., 34, 127 (1987).

The effect of polyol types of comparable molecular weights on tensile properties, pencil hardness and glass transition temperature (Tg) of cured films were determined and listed in Table III. The Tg was determined from the onset of thermomechanical analysis curves. The polydiethylene hexamethylenedicarbamate (SPU)-based autocurable oligomer has the highest Tg followed by polydiethylene maleate (UES) and polydiethylene succinate (SES)-based oligomers; the polyethylene glycol (PEG)-based sample having the lowest T. This trend is consistent with the chain flexibility of the various polyols.

TABLE III

| Type of oligomer | UM-PEG | UM-SES | UM-UES | UM-SPU |
|---|---|---|---|---|
| Gel content (%) | 91.7 | 91.0 | 90.4 | 90.0 |
| Pencil hardness* | B | HB | 2H | H |
| Tg of Cured film (°C.) | −10.5 | −0.5 | 4 | 5.5 |
| Young's modulus (kg/cm²) | 80 | 282 | 320 | 335 |
| Breaking strength | 64.7 | 80 | 102 | 108 |

TABLE III-continued

| Type of oligomer | UM-PEG | UM-SES | UM-UES | UM-SPU |
|---|---|---|---|---|
| (kg/cm²) | | | | |
| Elongation at break (%) | 128 | 110 | 96.3 | 165 |

*Pencil hardness is determined as a measure of surface hardness according to JIS K 5651.

The tensile properties of cured oligomers are also affected by polyol structure, for example, the SPU-based sample exhibit strong and tough properties with the highest breaking strength, Young's modulus and elongation at break. The trend of Young's modulus and breaking strength are in agreement with that of glass transition temperature for cured films, because decreasing Tg of cured films leads to a more flexible molecular chain and reduces the Young's modulus and breaking strength.

Example 3: Oligomer-Monomer Systems 8 oligomer-monomer systems were prepared by mixing 8 different monomers respectively with the UM-SPU oligomer prepared in Example 2 according to a weight ratio of oligomer/monomer=80/20.

The curing rates and various mechanical properties of these systems were determined by a similar proceduce as in Example 2 and the results were listed in Tables IV and V. The results were comparable.

TABLE IV

| | Gel Content, % | | | | |
|---|---|---|---|---|---|
| | Irradiation Time (s) | | | | |
| | 3 | 6 | 10 | 20 | 30 |
| HEMA | 10 | 20 | 46.9 | 88.7 | 89 |
| HEA | 77 | 80 | 81 | 87.7 | 90 |
| GMA | 6.5 | 16 | 31.8 | 85 | 87.7 |
| AMA | 67 | 76 | 82.2 | 87.7 | 90.1 |
| EGDMA | 16 | 37 | 64.2 | 84.5 | 87.7 |
| DEGDMA | 34.8 | 61 | 78.4 | 88 | 91 |
| TiEGDMA | 42.9 | 68 | 82 | 88 | 90.5 |
| TeEGDMA | 62.5 | 76 | 84 | 90 | 91 |

HEMA = hydroxyethyl methacrylate
HEA = hydroxyethyl acrylate
GMA = glycidyl methacrylate
AMA = dimethylaminoethyl methacrylate
EGDMA = ethylene glycol dimethacrylate
DEGDMA = diethylene glycol dimethacrylate
TiEGDMA = triethylene glycol dimethacrylate
TeEGDMA = tetraethylene glycol dimethacrylate

TABLE V

| Monomer | F | YM, kg/cm² | TS, kg/cm² | E, % | Tg, °C. |
|---|---|---|---|---|---|
| HEMA | 1 | 125 | 53 | 193 | −11.7 |
| HEA | 1 | 115 | 51 | 200 | −14.5 |
| GMA | 1 | 442 | 142 | 90 | 13.8 |
| AMA | 1 | 204 | 78 | 186 | −9.5 |
| EGDMA | 2 | 771 | 160 | 70 | 18.5 |
| DEGDMA | 2 | 626 | 154 | 88 | 13.5 |
| TiEGDMA | 2 | 520 | 150 | 113 | 10.2 |

TABLE V-continued

| Monomer | F | YM, kg/cm² | TS, kg/cm² | E, % | Tg, °C. |
|---|---|---|---|---|---|
| TeEGDMA | 2 | 420 | 140 | 135 | 6.5 |

*F = functionality;
YM = Young's modulus;
TS = tensile strength at break;
E = elongation at break.

We claim:

1. A radiation-autocurable oligomer having the following general formula

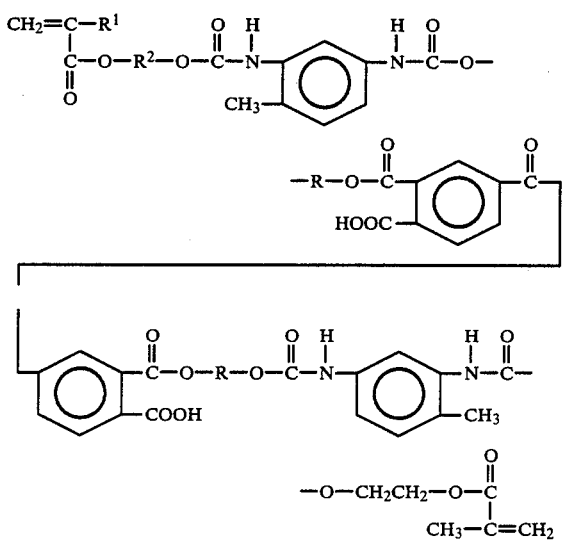

wherein
R¹ is a hydrogen or methyl group;
R² is a $C_1$–$C_4$ alkyl group; and
R represents the R in the polyol, HO-R-OH, having the following formula:

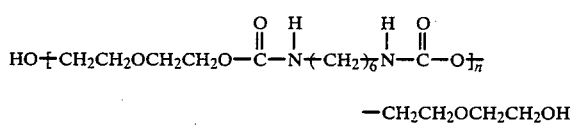

—CH₂CH₂OCH₂CH₂OH in which n is a number wherein the polyol has a number-average molecular weight ranging from about 300–800.

2. The radiation-autocurable oligomer of claim 1 wherein the R¹ is a methyl group.

3. The radiation-autocurable oligomer of claim 1 wherein the R² is an ethylene group.

4. The radiation-autocurable oligomer of claim 2 wherein the R² is an ethylene group.

5. A radiation-autocurable oligomer having the following general formula

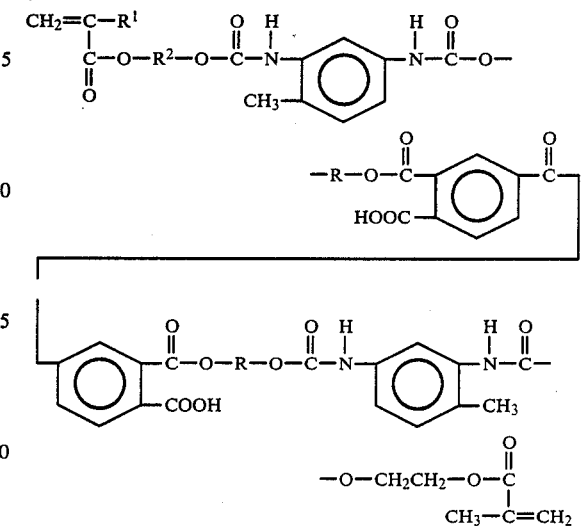

wherein
R¹ is hydrogen;
R² is CH₃; and
R represents the R in the polyol, HO-R-OH, having the following formula:

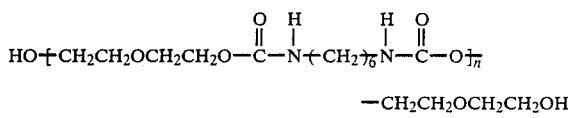

—CH₂CH₂OCH₂CH₂OH in which n is a number wherein the polyol has a number-average molecular weight of 400.

* * * * *